US011290553B2

United States Patent
(12) United States Patent
Ein-Gil et al.

(10) Patent No.: US 11,290,553 B2
(45) Date of Patent: Mar. 29, 2022

(54) USER-STRESS BASED NOTIFICATION SYSTEM

(71) Applicant: Intel Corporation, Santa Clara, CA (US)

(72) Inventors: Boaz Ein-Gil, Tzrufa (IL); Omri Mendels, Tel Aviv (IL); Alex Rapoport, Moshav Tal Shahar (IL)

(73) Assignee: Intel Corporation, Santa Clara, CA (US)

( * ) Notice: Subject to any disclaimer, the term of this patent is extended or adjusted under 35 U.S.C. 154(b) by 246 days.

(21) Appl. No.: 15/868,752

(22) Filed: Jan. 11, 2018

(65) Prior Publication Data

US 2019/0045020 A1 Feb. 7, 2019

(51) Int. Cl.

| | |
|---|---|
| ***H04L 29/08*** | (2006.01) |
| ***H04L 67/55*** | (2022.01) |
| ***A61B 5/16*** | (2006.01) |
| ***G06F 16/9535*** | (2019.01) |
| ***G06Q 10/10*** | (2012.01) |
| ***H04L 67/306*** | (2022.01) |
| *A61B 5/08* | (2006.01) |
| *A61B 3/11* | (2006.01) |
| *A61B 5/021* | (2006.01) |

(52) U.S. Cl.

CPC .............. *H04L 67/26* (2013.01); *A61B 5/165* (2013.01); *G06F 16/9535* (2019.01); *G06Q 10/10* (2013.01); *G06Q 10/109* (2013.01); *H04L 67/306* (2013.01); *A61B 3/112* (2013.01); *A61B 5/021* (2013.01); *A61B 5/0816* (2013.01)

(58) Field of Classification Search

CPC ....... H04L 67/26; H04L 67/306; A61B 5/165; A61B 5/021; A61B 3/112; A61B 5/0816; G06F 16/9535

USPC .......................................................... 709/206

See application file for complete search history.

(56) References Cited

U.S. PATENT DOCUMENTS

| | | | | |
|---|---|---|---|---|
| 10,051,107 | B1 * | 8/2018 | Prasad | H04M 1/72484 |
| 2011/0084795 | A1 * | 4/2011 | Fukuyori | |
| 2014/0007010 | A1 * | 1/2014 | Blom | G06F 3/0481<br>715/825 |

(Continued)

OTHER PUBLICATIONS

Liption, How to Repeat Local Notifications, Jan. 2017 (Year: 2017).*

(Continued)

*Primary Examiner* — Chris Parry

*Assistant Examiner* — Weiwei Y Stiltner

(74) *Attorney, Agent, or Firm* — Schwegman Lundberg & Woessner, P.A.

(57) ABSTRACT

A system for filtering device information to be provided to a user by a digital device or system according to physiological information collected from the user. The physiological information may be used to determine the user's present cognitive stress, wherein the device information may be prioritized, withheld, delayed, or deleted if the present cognitive stress exceeds a predetermined threshold. The device information may be further evaluated with contextual information such as different aspects of the device information or non-physiological user information (e.g. location, time of the day). The system may manage device information with minimal or less user interaction than user defined rule systems.

14 Claims, 3 Drawing Sheets

(56) References Cited

U.S. PATENT DOCUMENTS

| | | | | |
|---|---|---|---|---|
| 2015/0031942 | A1* | 1/2015 | Lashina | A61B 5/165 600/27 |
| 2015/0371516 | A1* | 12/2015 | Petersen | G08B 21/02 340/539.12 |
| 2018/0101776 | A1* | 4/2018 | Osotio | G06F 16/258 |
| 2018/0109482 | A1* | 4/2018 | DeLuca | H04L 51/32 |
| 2018/0143688 | A1* | 5/2018 | Rihn | A63F 13/285 |
| 2018/0174146 | A1* | 6/2018 | Bansal | G06Q 20/40145 |
| 2018/0248829 | A1* | 8/2018 | Hardee | H04L 51/24 |
| 2019/0373114 | A1* | 12/2019 | Gullander | H04M 1/72569 |

OTHER PUBLICATIONS

"Silence your device with Do Not Disturb", nexus, [Online] https://support.google.com/nexus/answer/6111295?hl=en Accessed on Apr. 11, 2018, (2018), 3 pgs.

"Use Do Not Disturb on your iPhone, iPad, and iPod touch", Apple Support, [online] https://support.apple.com/en-il/HT204321 Accessed on Apr. 11, 2018, (Nov. 2, 2017), 2 pgs.

Kahneman, Daniel, "Attention and Effort—Part 1 of 2", Prentice-Hall, Inc, Englewood Cliffs, (1973), 126 pgs.

Kahneman, Daniel, "Attention and Effort—Part 2 of 2", Prentice-Hall, Inc, Englewood Cliffs, (1973), 127pgs.

Klein, Kitty, et al., "Expressive Writing Can Increase Working Memory Capacity", Journal of Experimental Psychology vol. 130, No. 3, (Oct. 2001), 15 pgs.

Okoshi, Tadashi, et al., "Attelia: Reducing User's Cognitive Load due to Interruptive Notifications on Smart Phones", (2015), 9 pgs.

Setz, Cornelia, et al., "Discriminating Stress From Cognitive Load Using a Wearable EDA Device", IEEE Transactions On Information Technology in Biomedicine, vol. 14, No. 2, (Mar. 2010), 410-417.

* cited by examiner

USER-STRESS BASED NOTIFICATION SYSTEM

TECHNICAL FIELD

This document pertains generally, but not by way of limitation, to a notification system for filtering and scheduling notifications to wearable devices and other devices for capable of receiving notifications based on user stress.

BACKGROUND

Digital systems and devices are increasingly capable of interacting with users by providing notifications through a variety of signaling methods (tactile, vocal, visual, etc.). Wearable devices may further facilitate this interaction by receiving notification information from a plurality of digital systems and devices and pushing the notifications directly to the user's wrist, eyes, ears, or wherever the wearable device is worn on the user. However, with the increasing number of digital systems capable of providing notification information, the accumulation of information from multiple digital devices and systems may result in frequent or numerous notifications. The frequency and number of notifications may often exceed the user's expectations resulting in frustration, dissatisfaction, and even anger. The excessive or unwanted notifications may cause users to begin to habitually ignore notifications without considering the substance of the notification; partially or fully disable the notification capabilities of the device or system; or cease using the device or system altogether.

Specifically, when users are performing tasks requiring attentional control or effortful, the frequent and numerous notifications may act as a cognitive load where users must balance task demands and environmental demands. The resulting cognitive stress may impair the user's performance on cognitive tasks, such as episodic and working memory. The increasing amount of information pushed to users by digital systems and devices may overload a user's attention and lead to excessive interruptions. However, despite the increased cognitive loads and interruptions caused by pushed notifications, users often choose to endure the increased cognitive stress and distraction by preferring to retain the automatic notifications rather than obtaining the information manually.

Currently, a user may manually establish a set of rules on the communication device where the system will evaluate an incoming communication or notification against the predefined rules before notifying the user of the communication. The predefined rules may include defining quiet times where notifications of communications are automatically delayed until the end of the period and filtering communications based on the source (e.g., author, messaging system). Predefined rule systems may require users to manually establish a complex set of rules with multiple decisions and regularly maintain or update the rules based on changing needs, circumstances, or other conditions. The difficulty required to implement and maintain the system may be overwhelming and discourage users from implementing the system altogether.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present inventors have recognized, among other things, that a problem to be solved may include that the increased number and frequency of notifications from electronic devices and systems may overwhelm and distract users. However, the complexity and associated user maintenance of predefined rule systems for controlling notifications may discourage users from implementing or using the rule systems. In an example, the present subject matter may provide a solution to this problem, such as by filtering device information to be provided to a user by a digital device or system according to physiological information collected from the user. The physiological information may be used to determine the user's present physiological stress (which has documented impact on cognitive performance), wherein the device information may be prioritized, withheld, delayed, or deleted if the present stress level exceeds a predetermined threshold. The device information may be further evaluated with contextual information such as different aspects of the device information or non-physiological user information (e.g., location, time of the day). The system may manage device information with minimal or less user interaction than user-defined rule systems.

This overview is intended to provide an overview of subject matter of the present patent application. It is not intended to provide an exclusive or exhaustive explanation of the present subject matter. The detailed description is included to provide further information about the present patent application.

Figure 1:
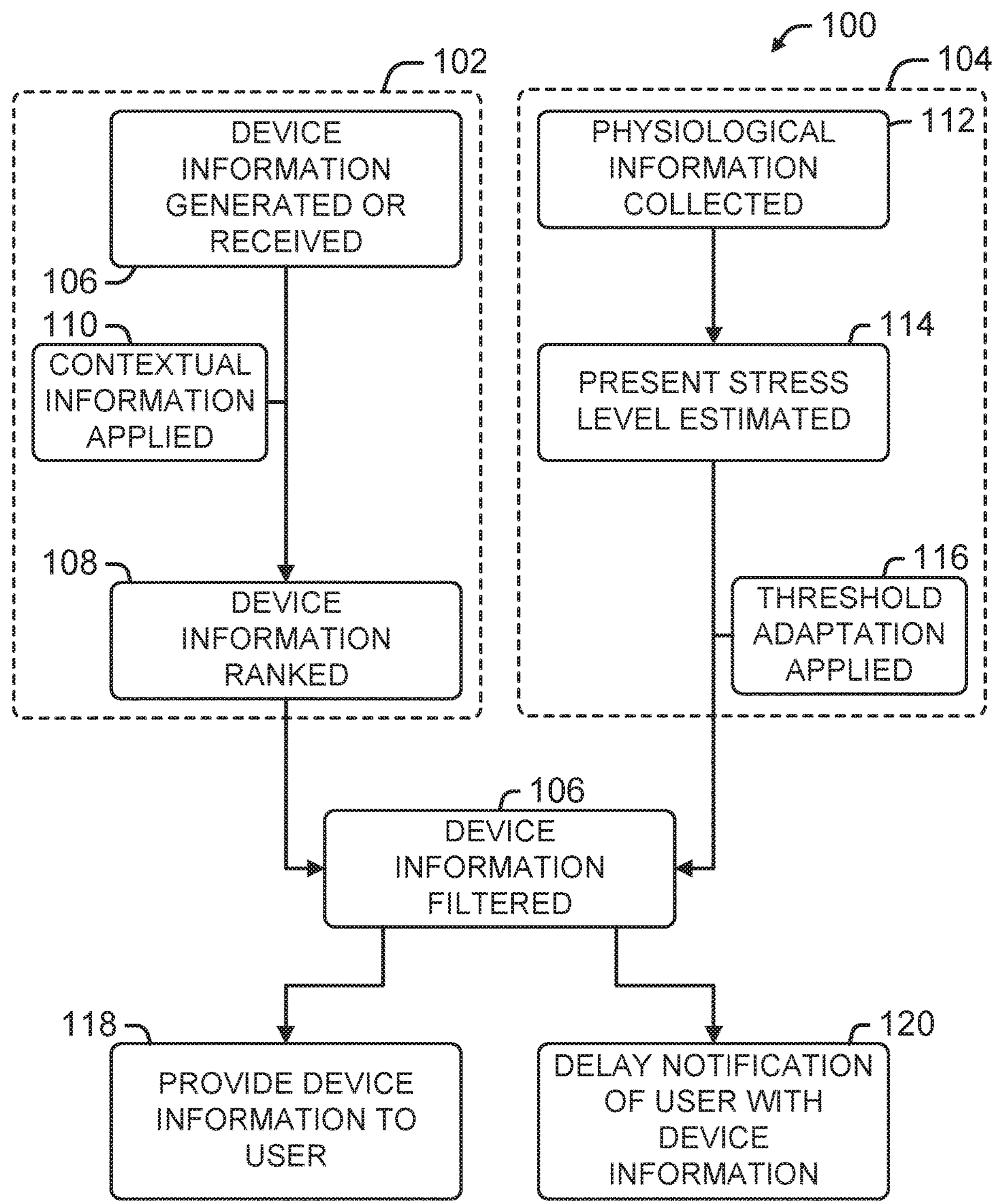
FIG. 1 is a schematic diagram of a system for filtering device information provided to a user according to an example of the present disclosure.

FIG. 1 is a schematic diagram of a system for filtering device information provided to a user according to an example of the present disclosure. As illustrated in FIG. 1, a system 100 for filtering device information provided to a user may comprise pre-evaluating device information 102, evaluating user stress levels 104, and filtering device information 106 based on the pre-evaluation of the device information and evaluated user stress levels.

Figure 2:
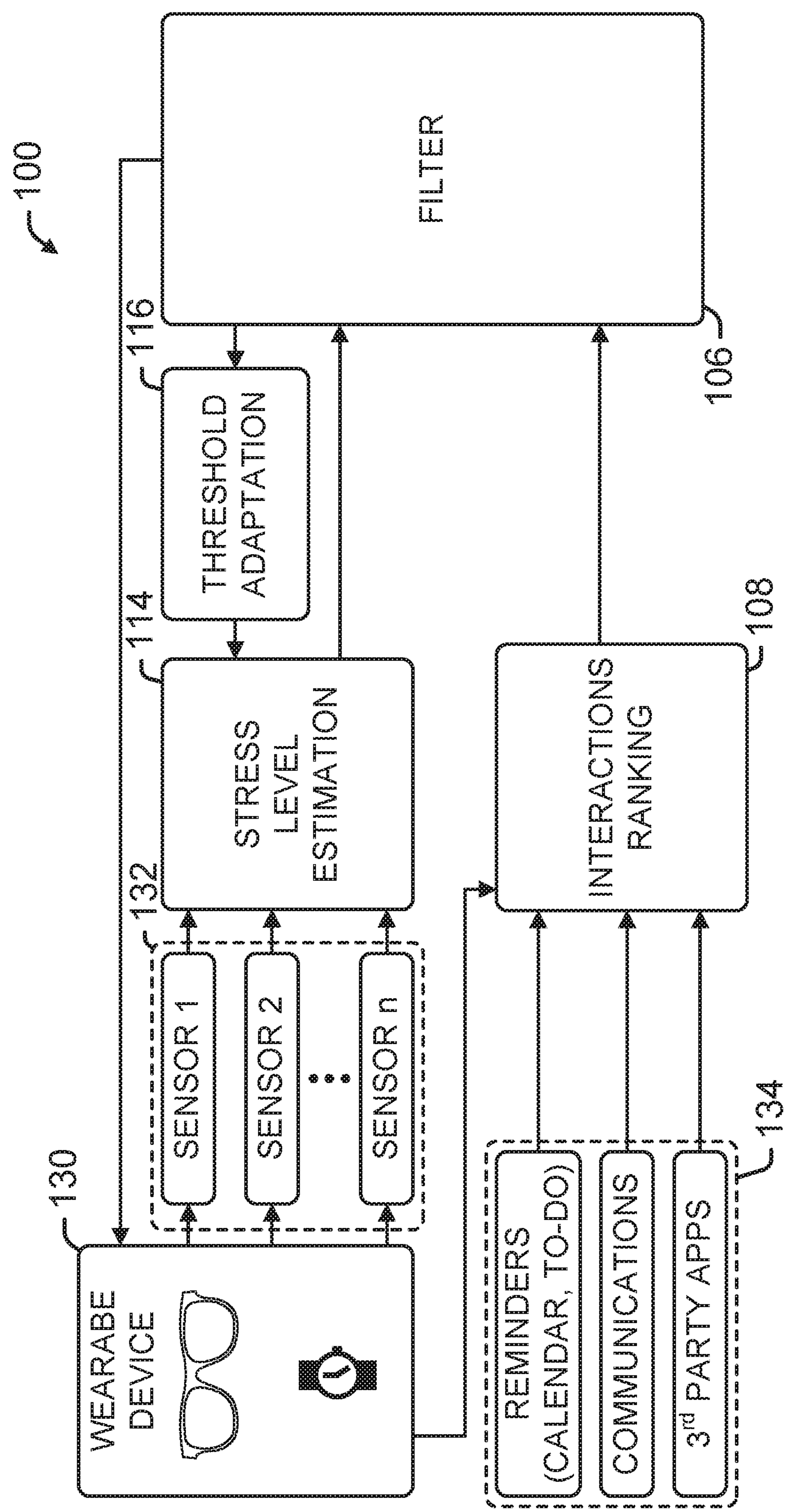
FIG. 2 is a schematic diagram of a device system for filtering device information provided to a user according to an example of the present disclosure.

The pre-evaluation of device information 102 may include generating and/or receiving device information 106 at a wearable device or other notification capable devices (e.g., mobile phone). As illustrated at FIG. 2, the device information may comprise reminders (calendar entries, to do lists, etc.); communications (entails, text messages, social media messages, alarm system, etc.); 3$^{rd}$ party app notifications; and notifications from other digital systems. The device information may also include, but is not limited to entails; instant messages; text messages; voicemails; general alerts or notifications (e.g., severe weather alerts); and notifications from automated systems or devices (e.g., wearable medical devices, home alarm systems). In an example, the device information may originate from the wearable or mobile device. In another example, the device information may originate with another digital device or system that is communicated to the wearable device.

In an example, the pre-evaluation of device information 102 may include ranking device information 108 that is generated and/or received at the wearable device 106. The ranking 108 the incoming device information may comprise evaluating different aspects specific to the incoming device information.

The ranking of the device information 108 may be determined at least in part based on the sender of the device information. The senders may be prioritized based on a machine-based algorithmic approach based on past user responses to device information from specific senders and/or world knowledge regarding the specific senders. In an example, entails or messages from certain senders (e.g., significant others, work superiors) may be more acceptable to users even at higher stress levels. Similarly, notifications from certain systems or devices (e.g., security systems, medical devices) may be more acceptable to users even at high-stress levels.

The ranking of device information 108 may be determined at least in part based on the type of device information. The type of information may be determined from the sender of the device information or the number of recipients. For example, personal messages from one individual to another individual or small group of individuals may be assigned a higher priority than a mass mailing. Similarly, more critical digital devices or systems (e.g., security systems, health monitoring systems) may be assigned a higher priority than information for less critical systems (e.g., home appliances).

The ranking of device information 108 may be determined at least in part based on the indicated urgency of the device information. If the device information is determined to be urgent, the device information may be assigned a higher priority. Certain metadata embedded within the device information may be used to flag the device information, which may be noted by the system 100 to identify the particular piece of device information as urgent. Similarly, the content of the device information may be evaluated by the system 100 for certain keywords (e.g., critical, urgent, ASAP) indicating the urgency of the information.

The ranking of device information 108 may be determined at least in part based on the rarity of the device information. Certain digital devices or systems are configured only to provide notifications in only rare or emergency situations (e.g., medical devices, home alarm systems). The system 100 may assign rarely provided device information at a higher priority as the user is more likely to be interested in the rarely sent device information, in contrast, to regularly provided, mundane device information.

In an example, the pre-evaluation of device information 102 may also include applying contextual information 110 not specific to the device information that is generated and/or received at the wearable device 106. The contextual information 110 may pertain to non-physiological information about the user including, but not limited to location; availability (e.g., in a meeting, on a call); time of day; previously, currently, or future scheduled events. In certain examples, the system may evaluate not only schedule events placed on the calendar, but anticipate that the user may be performing tasks on a to-do list and not placed on the calendar. The contextual information 110 may be used to in ranking the generated and/or received device information 108 with the specific contextual information related to the device information itself. In at least one embodiment, the contextual information 110 may be used to make a threshold evaluation on whether any device information is provided or whether all the device information is delayed.

In an example, the evaluation of user stress levels 104 may include collecting physiological information 112 from the user. The collection of physiological information 112 may include collecting physiological information with a mobile device, a wearable device, or another device having at least one sensor capable of collecting physiological information. The mobile or wearable device may comprise at least one sensor comprising, but not limited to a camera; an optical sensor; an accelerometer; a heart rate or pressure sensor; and a vibration sensor. Physiological information may include, but is not limited to heart rate; blood pressure; rapid or flax body motions; skin conductance; sweat secretions; silicon dioxide levels; eye pupil movement; insomnia or sleep cycles; and rapid or irregular breathing. In at least one example, the physiological information may relate to cognitive stress and be used to determine a present cognitive state and/or stress level of the user.

In an example, the evaluation of user stress levels 104 may include estimating the present stress level 114 of the user based on the collected physiological information 112. A stress level estimation module may receive the collected physiological information 112 and estimate the present stress level. The physiological information may include but is not limited to heart rate, body motion, skin conductance, and eye pupil movement. In an example, the estimation of the user's present stress level 114 may be performed on an "as needed" basis (e.g., immediately upon receiving device information). In another example, the user's stress level is continuously evaluated to provide a continuous baseline of the user's stress, wherein the user's present stress level 114 is compared to the continuous stress baseline to evaluate whether the user's present stress level 114 is elevated.

In an example, the evaluation of user stress levels 104 may include applying a threshold adaptation 116 to the user's present stress level 114. The user's present cognitive state or stress level may be compared against one or more stress thresholds to determine if the user's present stress level is elevated or in a state where device information may be unwanted or cause frustration. For the sake of simplicity, the user's present cognitive state or stress level is referred to as the stress level but may refer to the user's present cognitive state or stress level. In an example, a plurality of stress levels may be used so that the user's stress level may be categorized into one of a plurality of stress zones (e.g., no stress, low stress, medium stress, high stress).

In an example, the stress levels may be fixed at predetermined levels or may be learned automatically to tailor the system to the physiology of the individual user. The system may personalize the stress levels by evaluating the collected physiological information based on feedback from the user or past user behavior. Past user behavior may include whether the user is interested in or discards a specific piece of device information at a particular stress level. The user's prior responses to the specific piece of device information may be used to evaluate and update the predetermined stress thresholds. Similarly, if the user is not presented with a specific piece of device information at a particular stress level and the specific piece of device information was subsequently determined to be important, the predetermined stress thresholds may also be updated. The threshold learning may be performed statistically (e.g., estimating the probability of positive interaction with a specific piece of device information), with supervised machine learning approaches, or using reinforcement learning approaches. In at least one example, a user may manually update or set the different stress thresholds or select the types of device information appropriate at each stress zone.

In an example, the device information may be filtered 106 based on the pre-evaluation of the device information and evaluated user stress levels. The filter module 106 may evaluate the present stress level 114 with the threshold adaptation 116 applied with the specific and contextual device information 108,110 to determine whether to: (a) immediately provide the device information to the user 118, or (b) delay notification of the user with device information 120. In an example, the system 100 may vary the type of notification used to provide the device information (e.g., auditory, vibratory, visual, combinations thereof) based on the evaluated stress and device information specifics. For example, during high-stress times, a notification for less significant device information may be provided as a less conspicuous visual icon without auditory or vibratory cures, which allows the user to ignore the notification more readily.

A representative example of an application of the system described herein is receiving deuce information while driving. Certain driving situations may be high-stress situations (e.g., rush hour, urban driving, parking) where immediately provided device information may be unwanted. In this situation, the physiological indicators of the user's elevated stress and/or the vehicle motion may be detected by the wearable device. Low-priority or unimportant device information provided at this time may be temporarily delayed by the filtering module until the user's stress is lowered or the vehicle stops.

Another representative example of an application of the system described herein is receiving device information while approaching a deadline (e.g., scheduled meeting, deadline for the submission of work product). In this situation, the physiological indicators of the user's elevated stress may be detected by the wearable device and low-priority or unimportant device information may be delayed by the filtering module until after the deadline passes. The filtering module may determine if the device information relates to the deadline and immediately provide the relevant device information. For example, the system may delay information unrelated to an upcoming meeting (e.g., future scheduled events) and immediately forward information related to the upcoming meeting (e.g., rescheduling of the meeting).

As illustrated in FIG. 2, a system 100 for evaluating and filtering device information provided to a user may comprise a wearable device 130 or notification capable device (e.g., mobile device). The wearable device 130 may comprise at least one sensor 132 for collecting at least one physiological information about the present state of the user. The sensor 132 may comprise, but is not limited to a camera; an optical sensor; an accelerometer; a heart rate or pressure sensor; or a vibration sensor. The wearable device 130 may be configured to present device information 134 to the user as one or more notifications. The wearable device 130 may comprise at least one of a display, light, vibrating element, speaker, and combinations thereof operable to convey the device information to the user. The device information 134 may comprise reminders (calendar entries, to do lists, etc.); communications (email s, text messages, social media messages, alarm system, etc.); 3$^{rd}$ party app notifications; and notifications from other digital systems. In an example, the device information 134 may originate from the wearable or mobile device 130. In another example, the device information 134 may originate with another digital device or system communicating with the wearable device 130.

Figure 3:
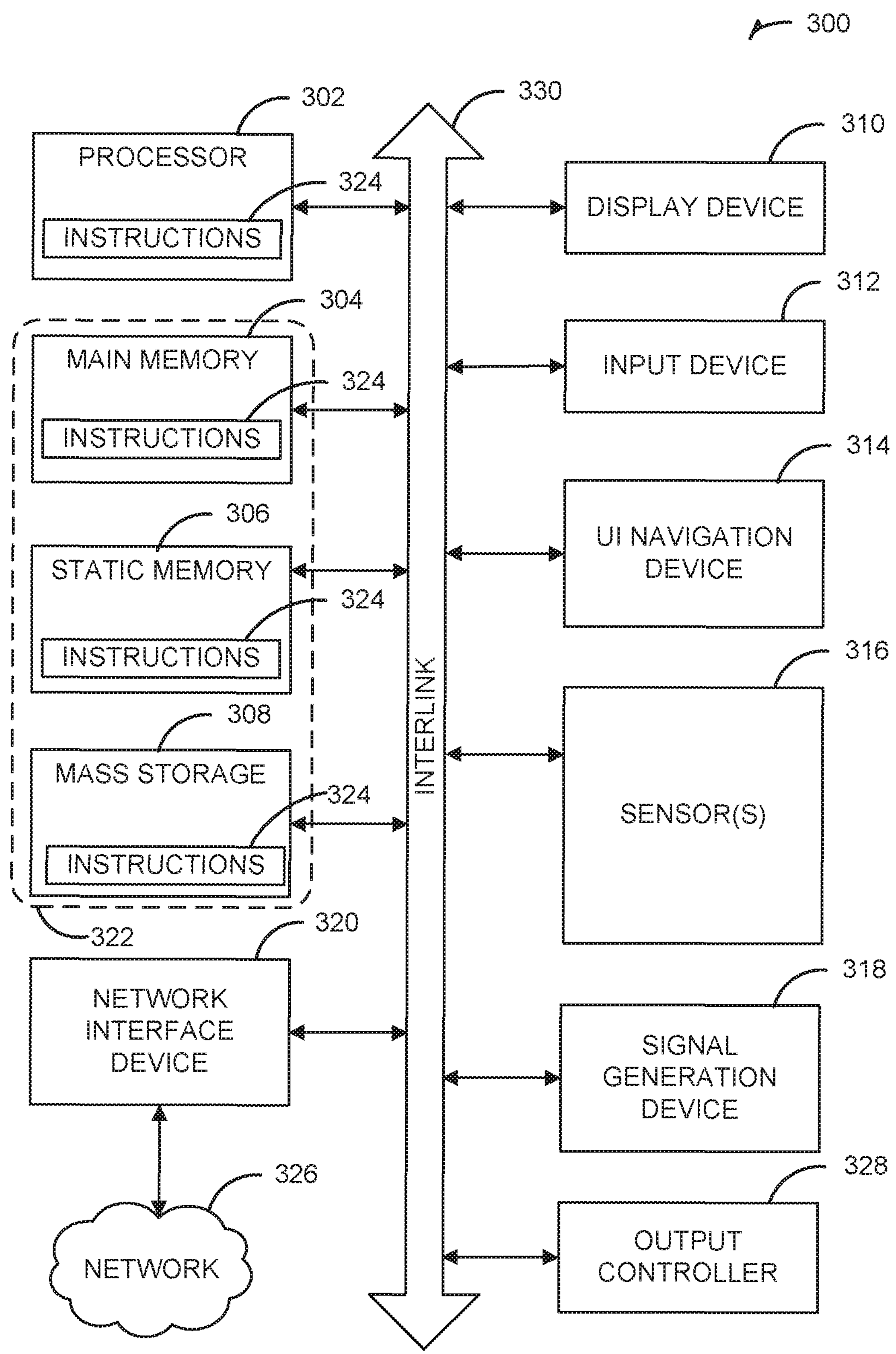
FIG. 3 is a block diagram illustrating an example of a machine upon which one or more embodiments may be implemented.

FIG. 3 illustrates a block diagram of an example machine 300 upon which any one or more of the techniques (e.g., methodologies) discussed herein may perform. Examples, as described herein, may include, or may operate by, logic or some components, or mechanisms in the machine 300. Circuitry (e.g., processing circuitry) is a collection of circuits implemented intangible entities of the machine 300 that include hardware (e.g., simple circuits, gates, logic, etc.). Circuitry membership may be flexible over time. Circuitries include members that may, alone or in combination, perform specified operations when operating. In an example, the hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components concerning the machine 300 follow.

In alternative embodiments, the machine 300 may operate as a standalone device or may be connected (e.g., networked) to other machines. In a networked deployment, the machine 300 may operate in the capacity of a server machine, a client machine, or both in server-client network environments. In an example, the machine 300 may act as a peer machine in peer-to-peer (P2P) (or other distributed) network environment. The machine 300 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 300 may include a hardware processor 302 (e.g., a central processing unit (CPU), a graphics processing unit (GPU), a hardware processor core, or any combination thereof), a main memory 304, a static memory (e.g., memory or storage for firmware, microcode, a basic-input-output (BIOS), unified extensible firmware interface (UEFI), etc.) 306, and mass storage 308 (e.g., hard drive, tape drive, flash storage, or other block devices) some or all of which may communicate with each other via an interlink (e.g., bus) 330. The machine 300 may further include a display unit 310, an alphanumeric input device 312 (e.g., a keyboard), and a user interface (UI) navigation device 314 (e.g., a mouse). In an example, the display unit 310, input device 312 and UI navigation device 314 may be a touch screen display. The machine 300 may additionally include a storage device (e.g., drive unit) 308, a signal generation device 318 (e.g., a speaker), a network interface device 320, and one or more sensors 316, such as a global positioning system (GPS) sensor, compass, accelerometer, or other sensor. The machine 300 may include an output controller 328, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 302, the main memory 304, the static memory 306, or the mass storage 308 may be, or include, a machine-readable medium 322 on which is stored one or more sets of data structures or instructions 324 (e.g., software) embodying or utilized by any one or more of the techniques or functions described herein. The instructions 324 may also reside, completely or at least partially, within any of registers of the processor 302, the main memory 304, the static memory 306, or the mass storage 308 during execution thereof by the machine 300. In an example, one or any combination of the hardware processor 302, the main memory 304, the static memory 306, or the mass storage 308 may constitute the machine-readable media 322. While the machine-readable medium 32,2, is illustrated as a single medium, the term "machine-readable medium" may include a single medium, or multiple media (e.g., a centralized or distributed database, and/or associated caches and servers) configured to store the one or more instructions 324.

The term "machine-readable medium" may include any medium that is capable of storing, encoding, or carrying instructions for execution by the machine 300 and that cause the machine 300 to perform any one or more of the techniques of the present disclosure, or that is capable of storing, encoding or carrying data structures used by or associated with such instructions. The non-limiting machine-readable medium examples may include solid-state memories, optical media, magnetic media, and signals (e.g., radio frequency signals, other photon based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 324 may be further transmitted or received over a communications network 326 using a transmission medium via the network interface device 320 utilizing any one of a number of transfer protocols (e.g., frame relay, Internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 320 may include one or more physical jacks (e.g., Ethernet, coaxial, or phone jacks) or one or more antennas to connect to the communications network 326. In an example, the network interface device 320 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 300, and includes digital or analog communications signals or another intangible medium to facilitate communication of such software. A transmission medium is a machine-readable medium.

Various Notes & Examples

Example 1 is a wearable device wearable by a user for managing information received by the wearable device for presentation to a user, comprising: a notification module to present the information to the user; a sensor to collect physiological information from the user corresponding to a present state of the user; and a controller to determine a present stress level of the user and evaluate the information provided to the notification module for presentation to the user according to the present stress level; and wherein the controller is to perform at least one of forward, prioritize, withhold, delay, or skip the presentation of the information to the user by the notification module.

In Example 2, the subject matter of Example 1 includes, wherein the information comprises at least one of reminders, emails, instant messages, text messages, voicemails, general alerts, automated notifications, third party app notifications, and combinations thereof.

In Example 3, the subject matter of Examples 1-2 includes, wherein the controller is to rank information as received on the digital device.

In Example 4, the subject matter of Example 3 includes, wherein the information includes a plurality of information and the controller is to rank information according to sender information; wherein the sender information comprises at least one of sending person, sending device, or prior user responses to sending person or device.

In Example 5, the subject matter of Examples 3-4 includes, wherein the controller is to rank each information of the plurality of information according to the number of recipients for each information of the plurality of information.

In Example 6, the subject matter of Examples 3-5 includes, wherein the controller ranks each information of the plurality of information according to an indicated urgency for each information of the plurality of information.

In Example 7, the subject matter of Examples 3-6 includes, wherein the controller ranks each information of the plurality of information according to a commonality factor of each information of the plurality of information; wherein the commonality factor is based on the frequency of that information of the plurality of information.

In Example 8, the subject matter of Examples 3-7 includes, a context module to apply contextual information to each information of the plurality of information and ranking each information of the plurality of information according to the contextual information; wherein the contextual information comprises at least one of location, availability, time of day, scheduled events, and combinations thereof.

In Example 9, the subject matter of Examples 1-8 includes, a digital system is integral to the wearable device.

In Example 10, the subject matter of Example 9 includes, a receiver module to receive information from the digital system, wherein the digital system is on a remote device positioned remote from the wearable device.

In Example 11, the subject matter of Example 10 includes, wherein the receiver module is configured to receive information via at least one of serial, parallel, or other wired or wireless forms of communication.

In Example 12, the subject matter of Examples 1-11 includes, wherein the notification module comprises at least one of a display, a light, a vibrating element, or a speaker, operable to convey the information to the user.

In Example 13, the subject matter of Example 12 includes, wherein the notification module is configured to provide a first type of notification to the user for a specific information if the present stress level of the user is below the predetermined threshold.

In Example 14, the subject matter of Example 13 includes, wherein the notification module is configured to provide a second type of notification to the user for the specific information if the present stress level of the user exceeds the predetermined threshold.

In Example 15, the subject matter of Example 14 includes, wherein the first and second types of notification are at least one of a visual, auditory, and vibratory cue; wherein the first and second type of notification are different.

In Example 16, the subject matter of Examples 1-15 includes, wherein the sensor comprises at least one of a camera, an optical sensor, an accelerometer, a heart rate or pressure sensor, a vibration sensor, and combinations thereof.

In Example 17, the subject matter of Example 16 includes, wherein the physiological information can comprise at least one of heart rate, blood pressure, irregular body motions, skin conductance, sweat secretions, silicon dioxide levels, irregular eye pupil movement, and sleep cycle information.

In Example 18, the subject matter of Examples 1-17 includes, wherein physiological information is continuously collected to create a continuous base line of user stress based on the collected physiological information.

In Example 19, the subject matter of Example 18 includes, wherein the present stress level is compared to the continuous base line of user stress; wherein the controller is configured to perform at least one of withhold, delay, or skip the information from the notification module if the present stress level exceeds the continuous base line of user stress.

In Example 20, the subject matter of Examples 1-19 includes, wherein the present stress level is compared to a plurality of stress thresholds to determine which stress threshold of the plurality of stress thresholds are exceeded by the present stress level; wherein whether the presentation of information is forwarded, prioritized, withheld, delayed, or skipped is determined according to which stress threshold of the plurality of predetermined stress thresholds is exceeded by the present stress level.

In Example 21, the subject matter of Example 20 includes, wherein the plurality of stress thresholds are predetermined and fixed.

In Example 22, the subject matter of Examples 20-21 includes, wherein the plurality of stress thresholds are personalized based on user feedback.

In Example 23, the subject matter of Examples 20-22 includes, wherein the plurality of stress thresholds are personalized based on at least one of statistics, supervised machine learning approaches, and reinforcement learning approaches.

In Example 24, the subject matter of Examples 20-23 includes, wherein the plurality of stress thresholds are personalized based on past user behavior; wherein the past user behavior includes whether the controller has been overridden to force the notification module to present the information to the user.

In Example 25, the subject matter of Examples 20-24 includes, wherein a present cognitive stress factor is determined based on the position of the present state of the user within the plurality of stress thresholds.

Example 26 is a method of managing information received on a digital device for a user, comprising: collecting, from a sensor, physiological information from the user corresponding to a present state of the user; determining a present stress level of the user from the collected physiological information corresponding to the present state of the user; filtering the information presented to the user according to the present stress level of the user; and wherein filtering the information comprises at least one of forwarding, prioritizing, withholding, delaying, or skipping presentation of the information to the user.

In Example 27, the subject matter of Example 26 includes, wherein the information comprises at least one of reminders, emails, instant messages, text messages, voicemails, general alerts, automated notifications, third party app notifications, and combinations thereof.

In Example 28, the subject matter of Examples 26-27 includes, ranking information as received on the digital device.

In Example 29, the subject matter of Example 28 includes, wherein the information includes a plurality of information and ranking information comprises ranking each information according to sender information; wherein the sender information comprises at least one of sending person, sending device, prior user responses to sending person or device, and combinations thereof.

In Example 30, the subject matter of Examples 28-29 includes, wherein ranking each information of the plurality of information comprises ranking each information according to the number of recipients for each information of the plurality of information.

In Example 31, the subject matter of Examples 28-30 includes, wherein ranking each information of the plurality of information comprises ranking each information according to an indicated urgency for each information of the plurality of information.

In Example 32, the subject matter of Examples 28-31 includes, wherein ranking each information of the plurality of information comprises ranking each information according to a commonality factor of each information of the plurality of information; wherein the commonality factor is based on the frequency of the information of the plurality of information.

In Example 33, the subject matter of Examples 28-32 includes, applying contextual information to each information of the plurality of information; and ranking each information of the plurality of information according to the contextual information; wherein the contextual information comprises at least one of location, availability, time of day, scheduled events, and combinations thereof.

In Example 34, the subject matter of Examples 26-33 includes, wherein the digital device comprises a digital system is integral to the wearable device.

In Example 35, the subject matter of Example 34 includes, wherein the digital system is on a remote device positioned remote from the wearable device.

In Example 36, the subject matter of Example 35 includes, receiving information via at least one of serial, parallel, or other wired or wireless forms of communication.

In Example 37, the subject matter of Examples 26-36 includes, wherein the notification module comprises at least one of a display, a light, a vibrating element, a speaker, and combinations thereof operable to convey the information to the user.

In Example 38, the subject matter of Example 37 includes, providing a first type of notification to the user for a specific information if the present stress level of the user is below the predetermined threshold.

In Example 39, the subject matter of Example 38 includes, providing a second type of notification to the user for a specific information if the present stress level of the user exceeds the predetermined threshold.

In Example 40, the subject matter of Example 39 includes, wherein the first and second types of notification are at least one of a visual, auditory, and vibratory cue; wherein the first and second type of notification are different.

In Example 41, the subject matter of Examples 26-40 includes, wherein the sensor comprises at least one of a camera, an optical sensor, an accelerometer, a heart rate or pressure sensor, a vibration sensor, and combinations thereof.

In Example 42, the subject matter of Example 41 includes, wherein the physiological information can comprise at least one of heart rate, blood pressure, irregular body motions, skin conductance, sweat secretions, silicon dioxide levels, irregular eye pupil movement, and sleep cycle information.

In Example 43, the subject matter of Examples 26-42 includes, continuously collecting physiological information; and creating a continuous base line of user stress based on the collected physiological information.

In Example 44, the subject matter of Example 43 includes, comparing the present stress level to the continuous base line of user stress; wherein the presentation of information is withheld, delayed, or skipped if the present stress level exceeds the continuous base line of user stress.

In Example 45, the subject matter of Examples 26-44 includes, determining which stress threshold of a plurality of stress threshold is exceeded by the present stress level; wherein whether the presentation of information is forwarded, prioritized, withheld, delayed, or skipped is determined according to which stress threshold of the plurality of predetermined stress thresholds is exceeded by the present stress level.

In Example 46, the subject matter of Example 45 includes, wherein the plurality of stress thresholds are predetermined and fixed.

In Example 47, the subject matter of Examples 45-46 includes, personalizing the plurality of stress thresholds based on user feedback.

In Example 48, the subject matter of Examples 45-47 includes, personalizing the plurality of stress thresholds based on at least one of statistics, supervised machine learning approaches, and reinforcement learning approaches.

In Example 49, the subject matter of Examples 45-48 includes, personalizing the plurality of stress thresholds based on past user behavior; wherein the past user behavior includes whether the controller has been overridden to force presentation of the information to the user.

In Example 50, the subject matter of Examples 45-49 includes, determining a present cognitive stress factor based on the position of the present state of the user within the plurality of stress thresholds.

Example 51 is an apparatus comprising means for performing any of the methods of Examples 26-50.

Example 52 is at least one machine-readable medium including instructions, which when executed by a machine, cause the machine to perform operations of any of the methods of Examples 26-50.

Example 53 is an apparatus for managing information received on a digital device for presentation to a user, comprising: means for collecting physiological information from the user corresponding to a present state of the user; means for determining a present stress level of the user from the collected physiological information corresponding to the present state of the user; means for filtering the information presented to the user according to the present stress level of the user; and wherein filtering the information comprises at least one of forwarding, prioritizing, withholding, delaying, or skipping presentation of the information to the user.

In Example 54, the subject matter of Example 53 includes, wherein the information comprises at least one of reminders, emails, instant messages, text messages, voicemails, general alerts, automated notifications, third party app notifications, and combinations thereof.

In Example 55, the subject matter of Examples 53-54 includes, means for ranking information as received on the digital device.

In Example 56, the subject matter of Example 55 includes, wherein the information includes a plurality of information and ranking information comprises ranking each information according to sender information; wherein the sender information comprises at least one of sending person, sending device, prior user responses to sending person or device, and combinations thereof.

In Example 57, the subject matter of Examples 55-56 includes, wherein ranking each information of the plurality of information comprises ranking each information according to the number of recipients for each information of the plurality of information.

In Example 58, the subject matter of Examples 55-57 includes, whey ranking each information of the plurality of information comprises ranking each information according to an indicated urgency for each information of the plurality of information.

In Example 59, the subject matter of Examples 55-58 includes, wherein ranking each information of the plurality of information comprises ranking each information according to the commonality factor of each information of the plurality of information; wherein the commonality factor is based on the frequency of that information of the plurality of information.

In Example 60, the subject matter of Examples 55-59 includes, means for applying contextual information to each information of the plurality of information; and means for ranking each information of the plurality of information according to the contextual information; wherein the contextual information comprises at least one of location, availability, time of day, scheduled events, and combinations thereof.

In Example 61, the subject matter of Examples 53-60 includes, wherein the apparatus further comprises a digital system is integral to the wearable device.

In Example 62, the subject matter of Example 61 includes, wherein the digital system is on a remote device positioned remote from the wearable device.

In Example 63, the subject matter of Example 62 includes, means for receiving information via at least one of serial, parallel, or other wired or wireless forms of communication.

In Example 64, the subject matter of Examples 53-63 includes, wherein the notification module comprises at least one of a display, a light, a vibrating element, a speaker, and combinations thereof operable to convey the information to the user.

In Example 65, the subject matter of Example 64 includes, means for providing a first type of notification to the user for a specific information if the present stress level of the user is below the predetermined threshold.

In Example 66, the subject matter of Example 65 includes, means for providing a second type of notification to the user for a specific information if the present stress level of the user exceeds the predetermined threshold.

In Example 67, the subject matter of Example 66 includes, wherein the first and second types of notification are at least one of a visual, auditory, and vibratory cue; wherein the first and second type of notification are different.

In Example 68, the subject matter of Examples 53-67 includes, wherein the sensor comprises at least one of a camera, an optical sensor, an accelerometer, a heart rate or pressure sensor, a vibration sensor, and combinations thereof.

In Example 69, the subject matter of Example 68 includes, wherein the physiological information can comprise at least one of heart rate, blood pressure, irregular body motions, skin conductance, sweat secretions, silicon dioxide levels, irregular eye pupil movement, and sleep cycle information.

In Example 70, the subject matter of Examples 53-69 includes, means for continuously collecting physiological information; and means for creating a continuous base line of user stress level based on the collected physiological information.

In Example 71, the subject matter of Example 70 includes, means for comparing the present state of the user to the continuous base line of user stress; wherein the controller is configured to perform at least one of withhold, delay, or skip the information from the notification module if the present stress level exceeds the continuous base line of user stress.

In Example 72, the subject matter of Examples 53-71 includes, means for determining which stress threshold of a plurality of stress threshold is exceeded by the present stress level; wherein whether the presentation of information is forwarded, prioritized, withheld, delayed, or skipped is determined according to which stress threshold of the plurality of predetermined stress thresholds is exceeded by the present stress level.

In Example 73, the subject matter of Example 72 includes, wherein the plurality of stress thresholds are predetermined and fixed.

In Example 74, the subject matter of Examples 72-73 includes, means for personalizing the plurality of stress thresholds based on user feedback.

In Example 75, the subject matter of Examples 72-74 includes, means for personalizing the plurality of stress thresholds based on at least one of statistics, supervised machine learning approaches, and reinforcement learning approaches.

In Example 76, the subject matter of Examples 72-75 includes, means for personalizing the plurality of stress thresholds based on past user behavior; wherein the past user behavior includes whether the controller has been overridden to force presentation of the information to the user.

In Example 77, the subject matter of Examples 72-76 includes, means for determining a present cognitive stress factor based on the position of the present state of the user within the plurality of stress thresholds.

Example 78 is a system for managing information received on a digital device for presentation to a user, wherein instructions for controlling operation of the system comprise instructions for: collecting, from a sensor, physiological information from the user corresponding to a present state of the user; determining a present stress level of the user from the collected physiological information corresponding to the present state of the user; filtering the information presented to the user according to the present stress level of the user; and wherein filtering the information comprises at least one of forwarding, prioritizing, withholding, delaying, or skipping presentation of the information to the user.

In Example 79, the subject matter of Example 78 includes, wherein information comprises at least one of reminders, entails, instant messages, text messages, voicemails, general alerts, automated notifications, third party app notifications, and combinations thereof.

In Example 80, the subject matter of Examples 78-79 includes, wherein instructions for controlling operation of the system comprise instructions for: ranking information as received on the digital device.

In Example 81, the subject matter of Example 80 includes, wherein the information includes a plurality of information and ranking information comprises ranking each information according to sender information; wherein the sender information comprises at least one of sending person, sending device, prior user responses to sending person or device, and combinations thereof.

In Example 82, the subject matter of Examples 80-81 includes, wherein ranking each information of the plurality of information comprises ranking each information according to the number of recipients for each information of the plurality of information.

In Example 83, the subject matter of Examples 80-82 includes, wherein ranking each information of the plurality of information comprises ranking each information according to an indicated urgency for each information of the plurality of information.

In Example 84, the subject matter of Examples 80-83 includes, wherein ranking each information of the plurality of information comprises ranking each information according to a commonality factor of each information of the plurality of information; wherein the commonality factor is based on the frequency of that information of the plurality of information.

In Example 85, the subject matter of Examples 80-84 includes, wherein instructions for controlling operation of the system comprise instructions for: applying contextual information to each information of the plurality of information; and ranking each information of the plurality of information according to the contextual information; wherein the contextual information comprises at least one of location, availability, time of day, scheduled events, and combinations thereof.

In Example 86, the subject matter of Examples 78-85 includes, wherein the digital system is integral to the wearable device.

In Example 87, the subject matter of Example 86 includes, wherein the digital system is on a remote device positioned remote from the wearable device.

In Example 88, the subject matter of Example 87 includes, wherein instructions for controlling operation of the system comprise instructions for: receiving information via at least one of serial, parallel, or other wired or wireless forms of communication.

In Example 89, the subject matter of Examples 78-88 includes, wherein the notification module comprises at least one of a display, a light, a vibrating element, a speaker, and combinations thereof operable to convey the information to the user.

In Example 90, the subject matter of Example 89 includes, wherein instructions for controlling operation of the system comprise instructions for: providing a first type of notification to the user for a specific information if the present stress level of the user is below the predetermined threshold.

In Example 91, the subject matter of Example 90 includes, wherein instructions for controlling operation of the system comprise instructions for: providing a second type of notification to the user for a specific information if the present stress level of the user exceeds the predetermined threshold.

In Example 92, the subject matter of Example 91 includes, wherein the first and second types of notification are at least one of a visual, auditory, and vibratory cue; wherein the first and second type of notification are different.

In Example 93, the subject matter of Examples 78-92 includes, wherein the sensor comprises at least one of a camera, an optical sensor, an accelerometer, a heart rate or pressure sensor, a vibration sensor, and combinations thereof.

In Example 94, the subject matter of Example 93 includes, wherein the physiological information can comprise at least one of heart rate, blood pressure, irregular body motions, skin conductance, sweat secretions, silicon dioxide levels, irregular eye pupil movement, and sleep cycle information.

In Example 95, the subject matter of Examples 78-94 includes, wherein instructions for controlling operation of the system comprise instructions for: continuously collecting physiological information; and creating a continuous base line of user stress based on the collected physiological information.

In Example 96, the subject matter of Example 95 includes, wherein instructions for controlling operation of the system comprise instructions for: comparing the present stress level to the continuous base line of user stress; wherein the presentation of information is withheld, delayed, or skipped if the present stress level exceeds the continuous base line of user stress.

In Example 97, the subject matter of Examples 78-96 includes, wherein instructions for controlling operation of the system comprise instructions for: determining which stress threshold of a plurality of stress threshold is exceeded by the present stress level; wherein whether the presentation of information is forwarded, prioritized, withheld, delayed, or skipped is determined according to which stress threshold of the plurality of predetermined stress thresholds is exceeded by the present stress level.

In Example 98, the subject matter of Example 97 includes, wherein the plurality of stress thresholds are predetermined and fixed.

In Example 99, the subject matter of Examples 97-98 includes, wherein instructions for controlling operation of the system comprise instructions for: personalizing the plurality of stress thresholds based on user feedback.

In Example 100, the subject matter of Examples 97-99 includes, wherein instructions for controlling operation of the system comprise instructions for: personalizing the plurality of stress thresholds based on at least one of statistics, supervised machine learning approaches, and reinforcement learning approaches.

In Example 101, the subject matter of Examples 97-100 includes, wherein instructions for controlling operation of the system comprise instructions for: personalizing the plurality of stress thresholds based on past user behavior; wherein the past user behavior includes whether the controller has been overridden to force presentation of the information to the user.

In Example 102, the subject matter of Examples 97-101 includes, wherein instructions for controlling operation of the system comprise instructions for: determining a present cognitive stress factor based on the position of the present state of the user within the plurality of stress thresholds.

Example 103 is at least one machine-readable medium including instructions that, when executed by processing circuitry, cause the processing circuitry to perform operations to implement of any of Examples 1-102.

Example 104 is an apparatus comprising means to implement of any of Examples 1-102.

Example 105 is a system to implement of any of Examples 1-102.

Example 106 is a method to implement of any of Examples 1-102.

Each of these non-limiting examples may stand on its own, or may be combined in any permutation or combination with any one or more of the other examples.

The above detailed description includes references to the accompanying drawings, which form a part of the detailed description. The drawings show, by way of illustration, specific embodiments in which the present subject matter may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feat ire is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the present subject matter should be determined with reference to the appended claims, along with the full scope of equivalents to which such claims are entitled.

What is claimed is:

1. A system for managing information received for presentation to a user, the system comprising:

a processor; and a non-transitory machine-readable medium including instructions for controlling operation of the system, which when executed by the processor, cause the processor to perform operations comprising:

collecting, from a sensor, physiological information from the user corresponding to a present state of the user;

determining a present stress level of the user from the collected physiological information corresponding to the present state of the user;

determining a priority of the information received for presentation to the user, wherein the priority is based on a rarity factor indicating that the information is rarely provided to the system;

determining which stress threshold of a plurality of stress thresholds is exceeded by the present stress level;

adjusting the plurality of stress thresholds based on past occurrences of whether the user keeps or discards information presented to the user at a particular stress level;

applying a filter to the information according to the present stress level of the user and the priority to obtain filtered information; and presenting the filtered information to the user according to which stress threshold of the plurality of stress thresholds is exceeded by the present stress level, wherein filtering the information comprises at least one of forwarding, prioritizing, withholding, delaying, or skipping presentation of the information to the user.

2. The system of claim 1, wherein instructions for controlling operation of the system comprise instructions for:

continuously collecting physiological information; and creating a continuous base line of user stress based on the collected physiological information.

3. The system of claim 2, wherein instructions for controlling operation of the system comprise instructions for:

comparing the present stress level to the continuous base line of user stress;

wherein the presentation of information is withheld, delayed, or skipped if the present stress level exceeds the continuous base line of user stress.

4. The system of claim 1, wherein instructions for controlling operation of the system comprise instructions for:

personalizing the plurality of stress thresholds based on past user behavior;

wherein the past user behavior includes whether a controller has been overridden to force presentation of the information to the user.

5. The system of claim 1, wherein instructions for controlling operation of the system comprise instructions for:

personalizing the plurality of stress thresholds based on at least one of statistics, supervised machine learning approaches, and reinforcement learning approaches.

6. A method of managing information received on a digital device for a user, comprising:

collecting, from a sensor, physiological information from the user corresponding to a present state of the user;

determining a present stress level of the user from the collected physiological information corresponding to the present state of the user;

determining a priority of the information received for presentation to the user, wherein the priority is based on a rarity factor indicating that the information is rarely provided;

determining which stress threshold of a plurality of stress thresholds is exceeded by the present stress level;

adjusting the plurality of stress thresholds based on past occurrences of whether the user keeps or discards information presented to the user at a particular stress level;

applying a filter to the information according to the present stress level of the user and the priority to obtain filtered information; and presenting the filtered information to the user according to which stress threshold of the plurality of stress thresholds is exceeded by the present stress level, wherein filtering the information comprises at least one of forwarding, prioritizing, withholding, delaying, or skipping presentation of the information to the user.

7. The method of claim 6, further comprising:

continuously collecting physiological information; and creating a continuous base line of user stress based on the collected physiological information.

8. The method of claim 7, further comprising:

comparing the present stress level to the continuous base line of user stress;

wherein the presentation of information is withheld, delayed, or skipped if the present stress level exceeds the continuous base line of user stress.

9. The method of claim 6, further comprising:

personalizing the plurality of stress thresholds based on past user behavior;

wherein the past user behavior includes whether a controller has been overridden to force presentation of the information to the user.

10. The method of claim 6, further comprising:

personalizing the plurality of stress thresholds based on at least one of statistics, supervised machine learning approaches, and reinforcement learning approaches.

11. A wearable device wearable by a user for managing information received by the wearable device for presentation to the user, comprising:

a sensor to collect physiological information from the user corresponding to a present state of the user; and a controller to:

determine a present stress level of the user;

determine a priority of the information received for presentation to the user, wherein the priority is based on a rarity factor indicating that the information is rarely provided;

determine which stress threshold of a plurality of stress thresholds is exceeded by the present stress level;

adjust the plurality of stress thresholds based on past occurrences of whether the user keeps or discards information presented to the user at a particular stress level;

apply a filter to the information according to the present stress level of the user and the priority to obtain filtered information; and present the filtered information to the user according to which stress threshold of the plurality of stress thresholds is exceeded by the present stress level, wherein the controller is to perform at least one of forward, prioritize, withhold, delay, or skip the presentation of the information to the user.

12. The wearable device of claim 11, wherein physiological information is continuously collected to create a continuous base line of user stress based on the collected physiological information.

13. The wearable device of claim 12, wherein the present stress level is compared to the continuous base line of user stress;

wherein the controller is configured to perform at least one of withhold, delay, or skip the information if the present stress level exceeds the continuous base line of user stress.

14. The wearable device of claim 11, wherein the plurality of stress thresholds is personalized based on past user behavior:

wherein the past user behavior includes whether the controller has been overridden to force presentation of the information to the user.

* * * * *

UNITED STATES PATENT AND TRADEMARK OFFICE

CERTIFICATE OF CORRECTION

PATENT NO. : 11,290,553 B2
APPLICATION NO. : 15/868752
DATED : March 29, 2022
INVENTOR(S) : Ein-Gil et al.

It is certified that error appears in the above-identified patent and that said Letters Patent is hereby corrected as shown below:

In the Claims

In Column 20, Line 27, in Claim 14, delete "behavior:" and insert --behavior;-- therefor Signed and Sealed this
Thirty-first Day of May, 2022

Katherine Kelly Vidal

Katherine Kelly Vidal
*Director of the United States Patent and Trademark Office*